US011147466B2

(12) United States Patent
Amemiya et al.

(10) Patent No.: US 11,147,466 B2
(45) Date of Patent: Oct. 19, 2021

(54) MAGNETIC RESONANCE IMAGING APPARATUS AND MAGNETIC RESONANCE IMAGE PROCESSING METHOD

(71) Applicant: Hitachi, Ltd., Tokyo (JP)

(72) Inventors: Tomoki Amemiya, Tokyo (JP); Suguru Yokosawa, Tokyo (JP); Yo Taniguchi, Tokyo (JP); Hisaaki Ochi, Tokyo (JP); Yoshihisa Sotome, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 897 days.

(21) Appl. No.: 15/911,289

(22) Filed: Mar. 5, 2018

(65) Prior Publication Data
US 2018/0338701 A1    Nov. 29, 2018

(30) Foreign Application Priority Data
May 26, 2017  (JP) .............................. JP2017-104077

(51) Int. Cl.
*A61B 5/055*    (2006.01)
*G01R 33/563*   (2006.01)
(Continued)

(52) U.S. Cl.
CPC .......... *A61B 5/055* (2013.01); *A61B 5/02007* (2013.01); *A61B 5/489* (2013.01);
(Continued)

(58) Field of Classification Search
CPC ... A61B 5/055; A61B 5/7267; A61B 5/02007; A61B 5/489; A61B 2576/02;
(Continued)

(56) References Cited

U.S. PATENT DOCUMENTS

| 5,332,968 A * | 7/1994 | Brown | G01R 33/56 |
| | | | 324/309 |
| 2005/0043614 A1* | 2/2005 | Huizenga | C23F 11/08 |
| | | | 600/427 |

(Continued)

FOREIGN PATENT DOCUMENTS

| JP | 2006-116299 A | 5/2006 |
| JP | 5395332 B2 | 1/2014 |

*Primary Examiner* — Sanjay Cattungal
(74) *Attorney, Agent, or Firm* — Crowell & Moring LLP

(57) ABSTRACT

A system is disclosed to simultaneously acquire a magnetic resonance angiography (MRA) image and a plurality of images in which the structure of a tissue other than a blood vessel can be ascertained without performing imaging for the MRA image, and to shorten a time of MR examination. Two or more kinds of physical property dependent images obtained from a nuclear magnetic resonance signal measured in accordance with a predetermined pulse sequence under a plurality of imaging conditions are combined using a predetermined combination function. At this time, a plurality of division regions are set in the physical property dependent image, and the combination parameter satisfying a condition that a difference between a pixel value of the specific tissue and a pixel value of a tissue other than the specific tissue increases is determined at each of the division regions in the actually measured two or more kinds of physical property dependent images, using standard data of the two or more kinds of physical property dependent images, and the combination parameter is used to combine the two or more kinds of images.

14 Claims, 12 Drawing Sheets

(51) Int. Cl.
  *G01R 33/561*  (2006.01)
  *G01R 33/56*  (2006.01)
  *A61B 5/00*  (2006.01)
  *A61B 5/02*  (2006.01)
  *G01R 33/54*  (2006.01)

(52) U.S. Cl.
  CPC ........ *A61B 5/7267* (2013.01); *G01R 33/5602* (2013.01); *G01R 33/5608* (2013.01); *G01R 33/5616* (2013.01); *G01R 33/5635* (2013.01); *A61B 5/0035* (2013.01); *A61B 2576/02* (2013.01); *G01R 33/546* (2013.01)

(58) Field of Classification Search
  CPC .............. A61B 5/0035; G01R 33/5608; G01R 33/5602; G01R 33/5635; G01R 33/5616; G01R 33/546; G16H 50/70; G16H 30/40
  See application file for complete search history.

(56) References Cited

U.S. PATENT DOCUMENTS

| | | | |
|---|---|---|---|
| 2006/0064004 A1 | 3/2006 | Machida | |
| 2008/0119721 A1 | 5/2008 | Kimura et al. | |
| 2014/0226890 A1* | 8/2014 | O'Brien | G01R 33/5608 382/131 |
| 2014/0303478 A1* | 10/2014 | Roche | G01R 33/5608 600/410 |
| 2018/0095152 A1* | 4/2018 | Triaire | G01R 33/565 |

\* cited by examiner

[Fig. 1]
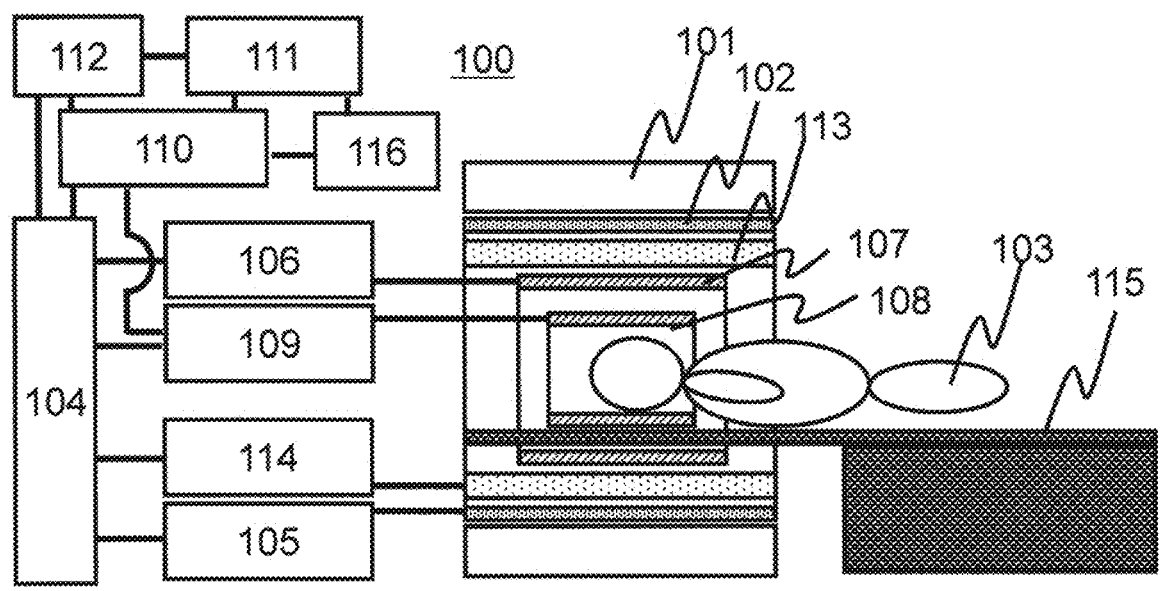

[Fig. 2]
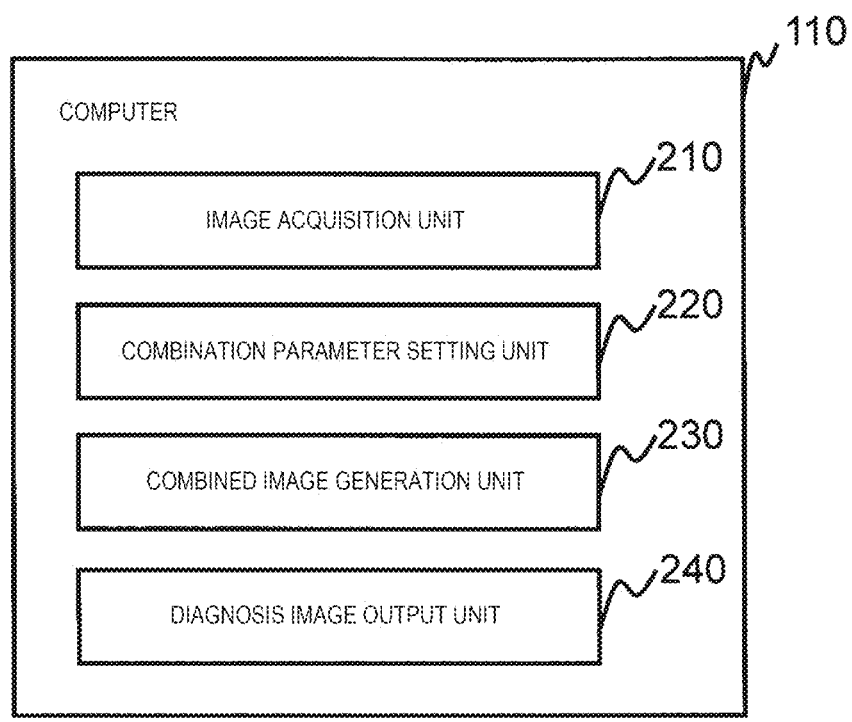

[Fig. 3A]
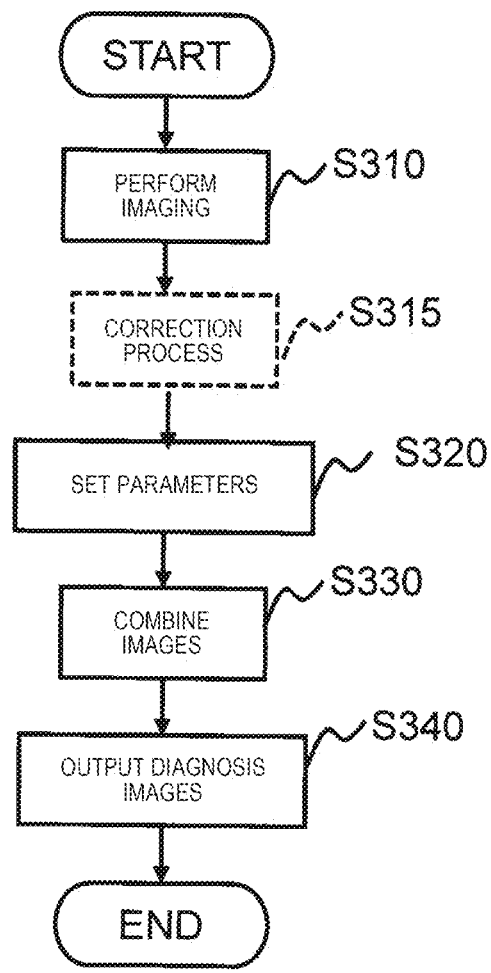

[Fig. 3B]
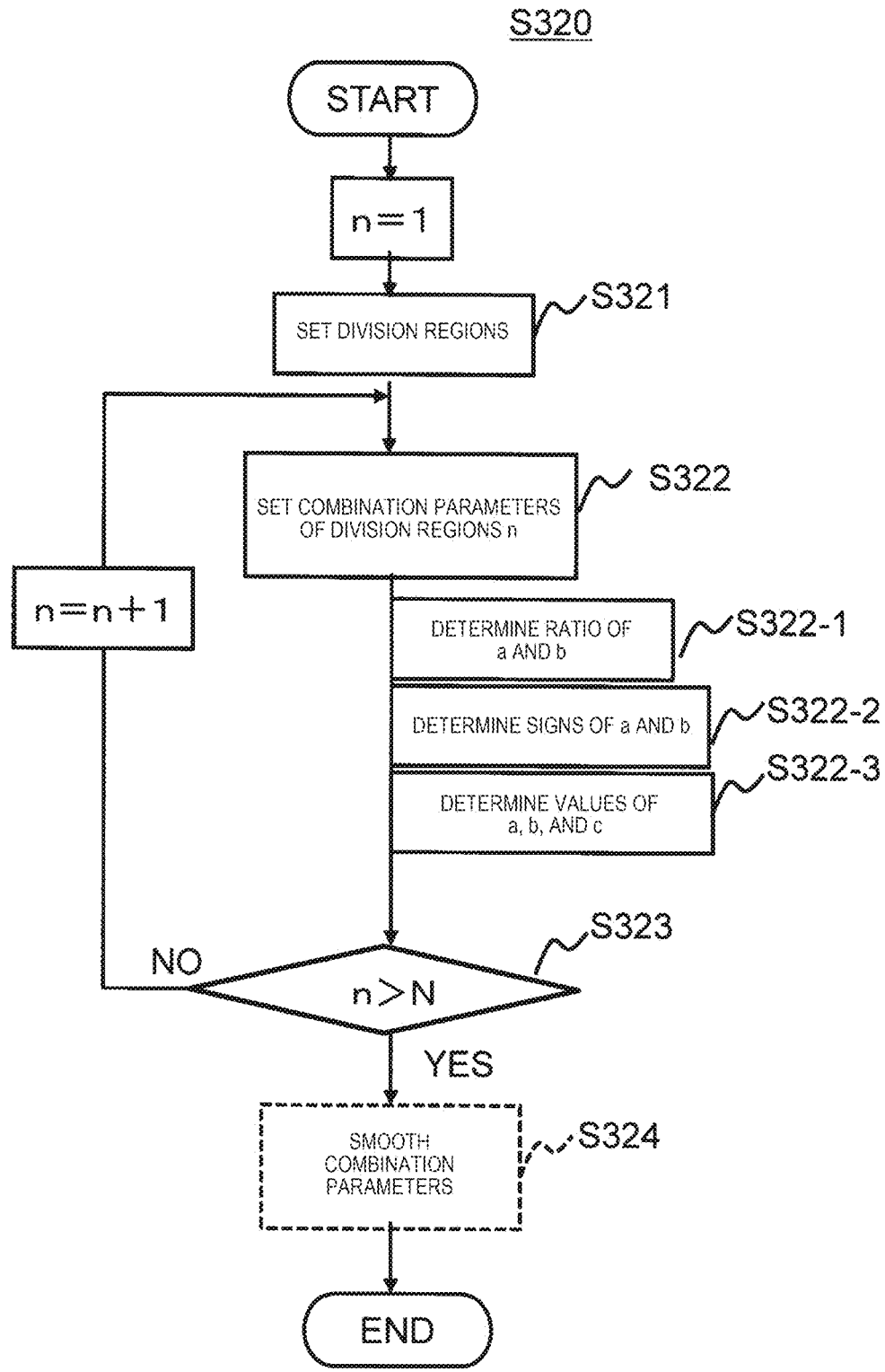

[Fig. 4A]
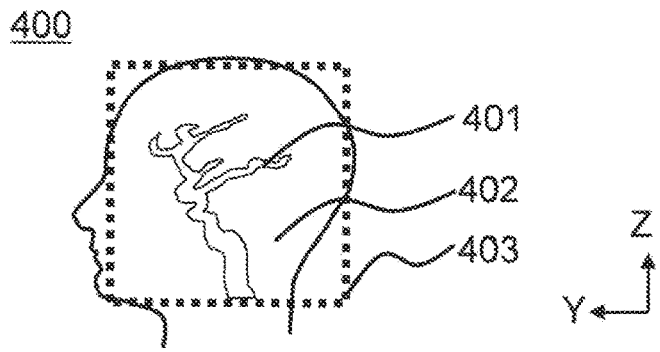
[Fig. 4B]
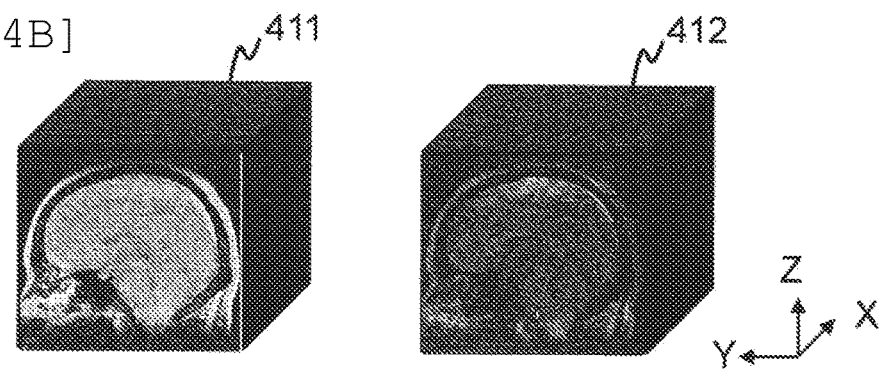
[Fig. 4C]
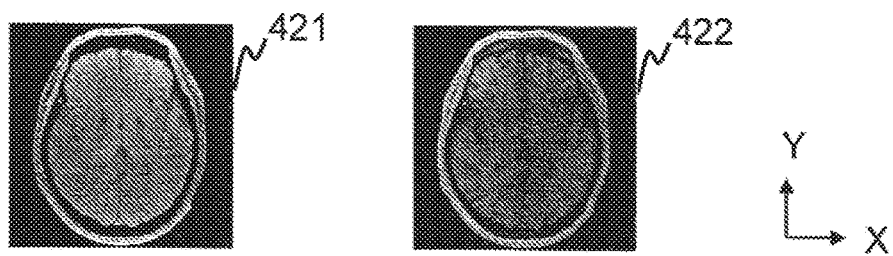
[Fig. 4D]
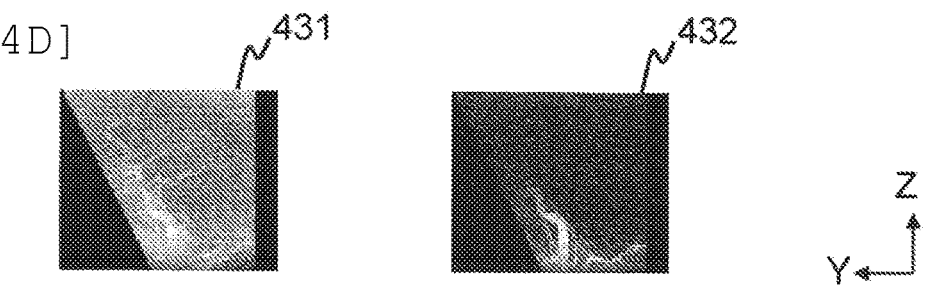
[Fig. 4E]
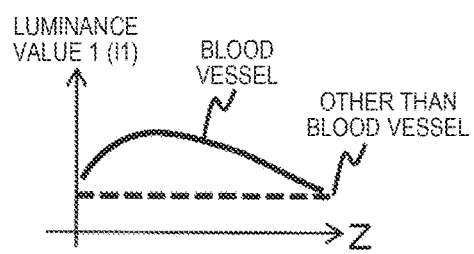
[Fig. 4F]
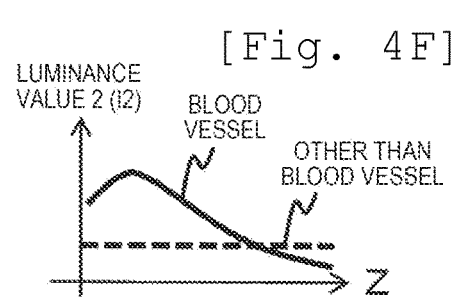

[Fig. 5A]
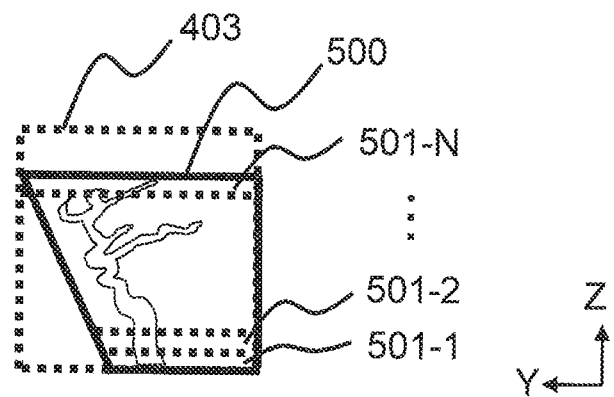
[Fig. 5B]
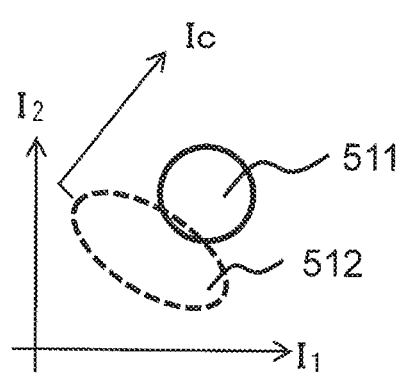
[Fig. 5C]
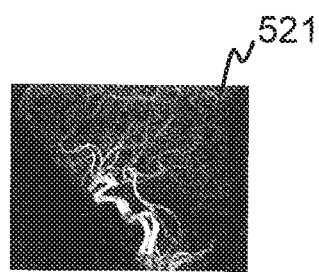

[Fig. 6]
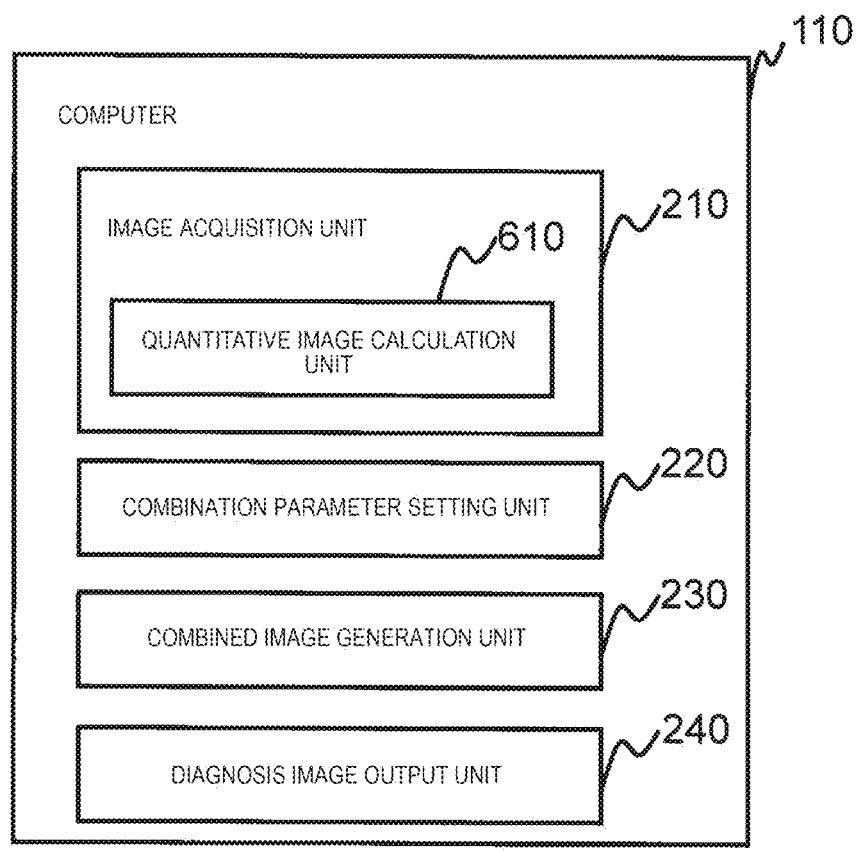

[Fig. 7]
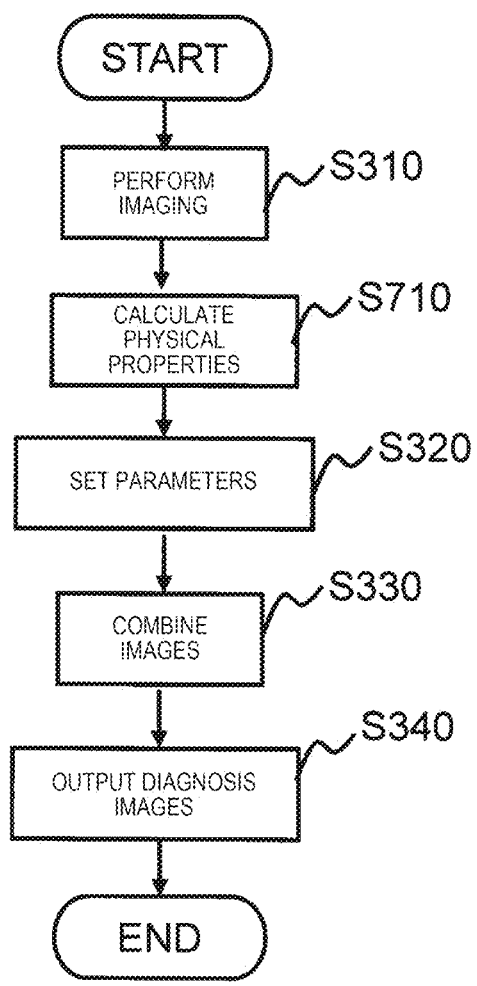

[Fig. 8]
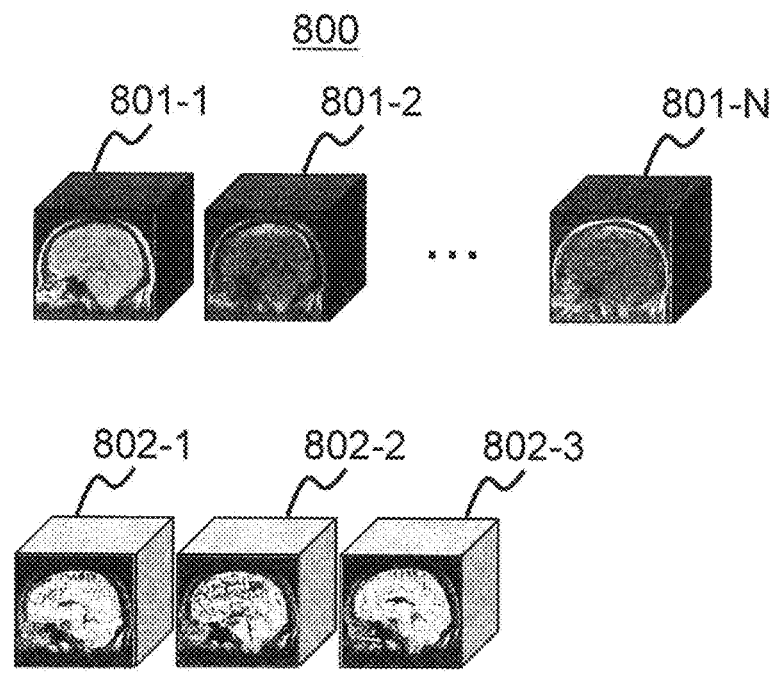

[Fig. 9]
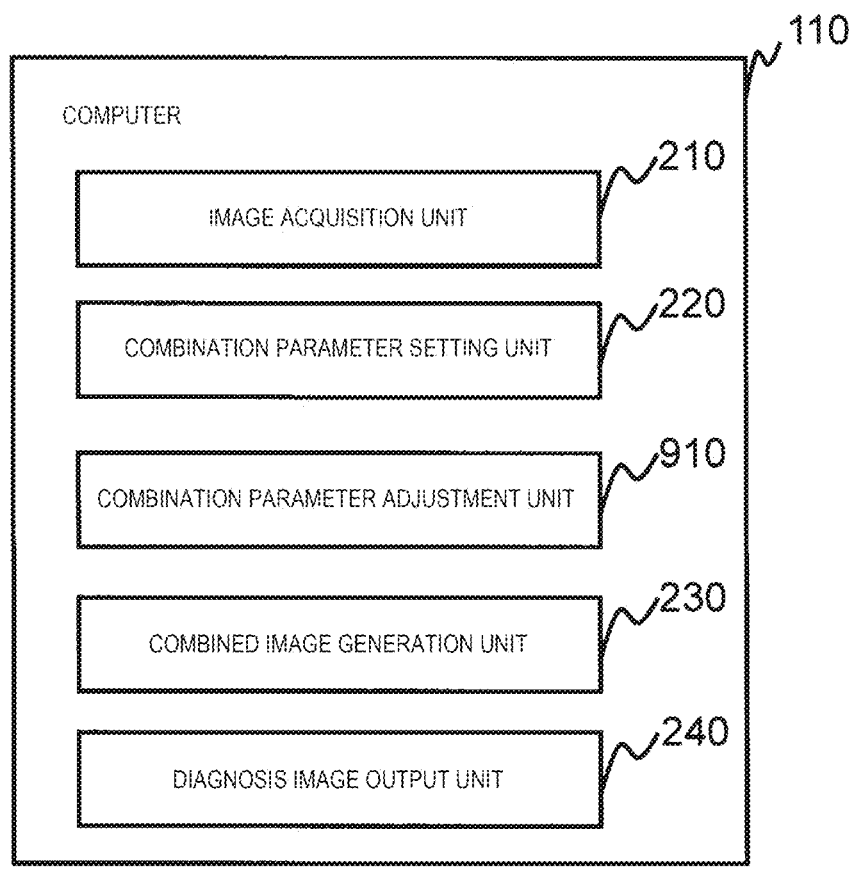

[Fig. 10]
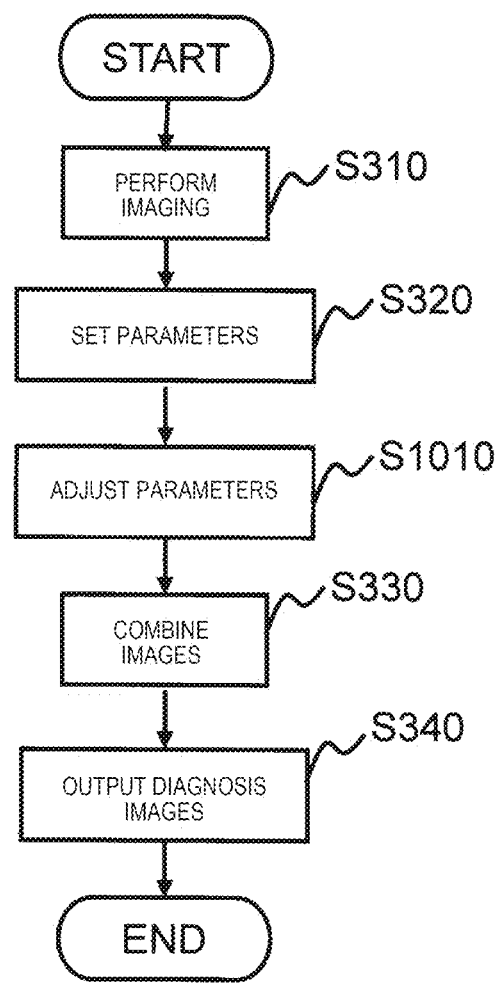

[Fig. 11]
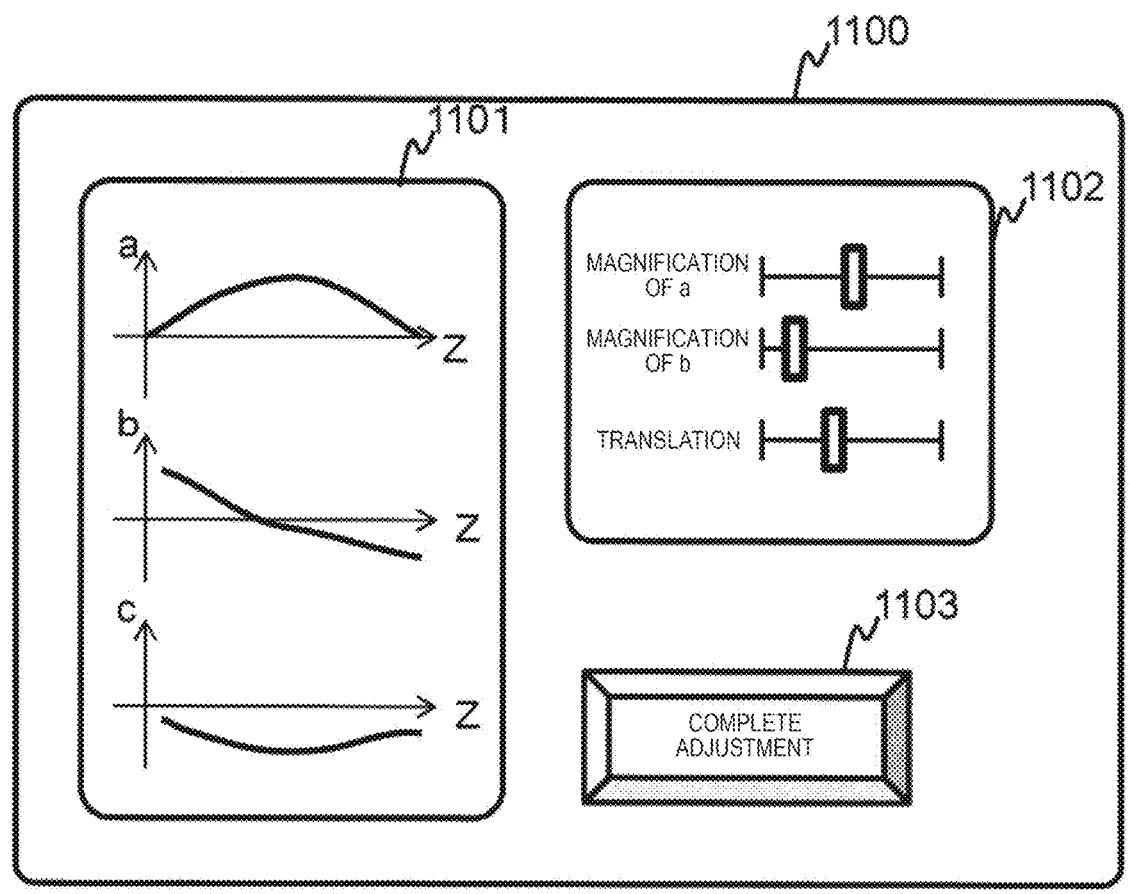

MAGNETIC RESONANCE IMAGING APPARATUS AND MAGNETIC RESONANCE IMAGE PROCESSING METHOD

TECHNICAL FIELD

The present invention relates to a magnetic resonance imaging (MRI) apparatus.

BACKGROUND ART

MRI apparatuses are medical image diagnostic apparatuses that mainly use a proton nuclear magnetic resonance phenomenon. MRI apparatuses can image any cross section of a subject in a noninvasive manner and can acquire information regarding biological functions such as a blood flow and metabolism in addition to morphological information.

In general, MRI apparatuses acquire weighted images in which relative differences in physical properties related to nuclear magnetic resonance of biological tissues, for example, a longitudinal relaxation time (T1), a transverse relaxation time (T2), and a proton density (PD) are weighted. Weighted degrees or target physical values can be changed in accordance with selected pulse sequences or imaging parameters.

In imaging of blood vessels, various magnetic resonance angiographies (hereinafter referred to as MRAs) have been developed. For example, there are known various methods such as a method using a phenomenon in which a portion to which blood flows inside an imaging region has higher luminance than other inactive tissues (time of flight: hereinafter referred to as a TOF method), an imaging scheme of causing phase rotation of nuclear magnetization which depends on a flow rate (phase contrast: hereinafter referred to as a PC method), and a method in which a blood vessel has low luminance using the fact that magnetic susceptibility of a blood vessel is different from magnetic susceptibility of a portion other than a blood vessel (blood sensitive imaging).

MRA, visualization abilities of a main portion and a peripheral portion are different from each other. Therefore, a scheme of imaging a plurality of MRA images and combining the images by calculation to generate an MRA image with good quality in which the shapes of blood vessels are easily ascertained has been proposed. For example, PTL 1 discloses a scheme of imaging MRA images in two different pulse sequences and substituting a part of one image with the other image. PTL 2 discloses a scheme of imaging an MRA image with good quality by imaging MRA images in which blood vessels have high luminance and low luminance in two different pulse sequences and taking a difference with a different coefficient for each pixel.

CITATION LIST

Patent Literature

PTL 1: JP-A-2006-116299
PTL 2: Japanese Patent No. 5395332

SUMMARY OF INVENTION

Technical Problem

An MRA image is captured, for example, by using pulse sequences in which blood vessels have higher luminance or lower luminance than tissues other than blood vessels and a difference in the luminance is as little as possible in tissues other than blood vessels or injecting a contrast agent. Therefore, an image is captured separately from a weighted image by which tissues other than blood vessels are diagnosed. Accordingly, in MR examination of a head in which imaging blood vessels are also requested in addition to various weighted images, a time taken to image the blood vessels is separately necessary in addition to a time taken to image the weighted images. Thus, there is a problem that a time for entire MR examination is longer.

In the methods disclosed in PTL 1 and PTL 2, MRA images with good quality can be obtained. However, in capturing of a plurality of images used for calculation, it is assumed that a pulse sequence for blood vessel imaging is used and imaging is performed so that a difference in luminance of tissues other than blood vessels is as little as possible. Therefore, apart from capturing of weighted images by which other tissues are diagnosed, it remains necessary to capture MRA images and the problem that a time for entire MR examination is longer may not be resolved.

The invention is devised in view of the foregoing circumstances and an object of the invention is to provide an imaging technology for capturing a plurality of weighted images by which the structure of the tissue other than the blood vessels can be ascertained and acquiring MRA images from the captured images by calculation to simultaneously acquire MRA images and a plurality of images by which a structure of tissues other than blood vessels can be ascertained and shorten a time of MR examination.

Solution to Problem

According to an aspect of the invention, a magnetic resonance imaging apparatus includes: an image acquisition unit that measures a nuclear magnetic resonance signal in accordance with a predetermined pulse sequence under a plurality of imaging conditions to acquire two or more kinds of images; a combined image generation unit that combines the two or more kinds of images using a predetermined combination parameter and a combination function to generate a combined image; and a combination parameter setting unit that sets a combination parameter to be used by the combined image generation unit. The combination parameter setting unit sets a plurality of division regions in the images acquired by the image acquisition unit and sets the combination parameter satisfying a condition that a difference between a pixel value of a specific tissue and a pixel value of a tissue other than the specific tissue is large based on standard data of the two or more kinds of images at each of the division regions.

Advantageous Effects of Invention

According to the invention, by setting the combination parameter at each division region in a specific tissue of which a pixel value can be switched in accordance with a region of a subject, for example, a blood vessel, and combining images, it is possible to simultaneously acquire an MRA image and an image in which the structure of a tissue other than the blood vessel can be ascertained. Thus, it is possible to shorten a time of MR examination.

BRIEF DESCRIPTION OF DRAWINGS

FIG. 1 is a block diagram illustrating a configuration of an MRI apparatus according to a first embodiment.

FIG. 2 is a block diagram illustrating a computer according to the first embodiment.

FIG. 3A is a flowchart illustrating an operation of the computer according to the first embodiment.

FIG. 3B is a flowchart illustrating the details of a part of a process of FIG. 3A.

FIG. 4A is an explanatory diagram illustrating a head and an imaged region of a subject, FIG. 4B is an explanatory diagram illustrating a 3-dimensional captured image, FIG. 4C is an explanatory diagram illustrating a cross sectional image of the 3-dimensional captured image, FIG. 4D is an explanatory diagram illustrating a projected drawing of a partial region of the 3-dimensional captured image, FIG. 4E is a graph illustrating average luminance of a blood vessel and a tissue other than blood vessel for each cross section in the Z direction in a 3-dimensional image 411, and FIG. 4F is a graph illustrating average luminance of a blood vessel and a tissue other than the blood vessel for each cross section in the Z direction in a 3-dimensional image 412.

FIG. 5A is an explanatory diagram illustrating forms of a region of interest and a division region set by a combination parameter setting unit, FIG. 5B is an explanatory diagram illustrating ranges of a blood vessel with pixel values $I_1$ and $I_2$ and a tissue other than the blood vessel inside a certain division region, and FIG. 5C is an explanatory diagram illustrating a combined image generated by a combined image generation unit.

FIG. 6 is a block diagram illustrating a computer according to the fourth embodiment.

FIG. 7 is a flowchart illustrating an operation of the computer according to the fourth embodiment.

FIG. 8 is an explanatory diagram illustrating an example of a physical property dependent image acquired by an image acquisition unit according to the fourth embodiment.

FIG. 9 is a block diagram illustrating a computer according to a fifth embodiment.

FIG. 10 is a flowchart illustrating an operation of the computer according to the fifth embodiment.

FIG. 11 is an explanatory diagram illustrating an example of a parameter adjustment screen according to the fifth embodiment.

DESCRIPTION OF EMBODIMENTS

Embodiments of the invention will be described with reference to the drawings. The invention is not limited thereto. Throughout all the drawings for describing the embodiments of the invention, the same reference numerals are given to the same functions unless otherwise mentioned and the repeated description thereof will be omitted.

<Configuration of Apparatus>

First, a configuration and an operation of an apparatus common to each embodiment will be described.

FIG. 1 illustrates a configuration of a typical MRI apparatus 100 to which the invention is applied. As illustrated in FIG. 1, the MRI apparatus 100 includes a magnet 101 that generates a static magnetic field, a gradient magnetic field coil 102 that generates a gradient magnetic field, an RF coil 107 that radiates a high-frequency magnetic field pulse to a subject (for example, a living body) 103, an RF probe 108 that detects an echo signal generated from the subject 103, and a bed (table) 115 on which the subject 103 is placed inside a space of the generated static magnetic field of the magnet 101.

The MRI apparatus 100 further includes a gradient magnetic field power supply 105 that drives the gradient magnetic field coil 102, a high-frequency magnetic field generator 106 that drives the RF coil 107, a receiver 109 that detects an echo signal detected with the RF probe 108, and a sequencer 104. The sequencer 104 sends a command to the gradient magnetic field power supply 105 and the high-frequency magnetic field generator 106, generates a gradient magnetic field and a high-frequency magnetic field, respectively, and sets a nuclear magnetic resonance frequency serving as a detection reference in the receiver 109. Each unit of the above-described MRI apparatus 100 is collectively referred to as a measurement unit.

In addition to the units, the MRI apparatus 100 includes a computer 110 that performs signal processing on a signal detected by the receiver 109, a display device 111 that displays a processing result in the computer 110, a storage device 112 that retains the processing result, and an input device 116 that receives an instruction from a user. The storage device 112 retains various kinds of data necessary for a process in the computer 110. The computer 110 includes a CPU and a memory and is configured to realize a function of each unit by software by allowing the CPU to read a program stored in the memory in advance and execute the program. Here, the computer 110 according to the embodiment is not limited to the realization of the functions by software. Some or all of the functions can also be realized by hardware such as a custom IC such as an application specific integrated circuit (ASIC) or a programmable IC such as a field programmable gate array (FPGA).

In a case in which it is necessary to adjust uniformity of the static magnetic field, the MRI apparatus 100 may further include a shim coil 113 and a shim power supply 114 that drives the shim coil 113. The shim coil 113 includes a plurality of channels and generates an additional magnetic field to correct non-uniformity of the static magnetic field by a current supplied from the shim power supply 114. The current allowing to each channel included in the shim coil 113 at the time of adjustment of the uniformity of the static magnetic field is controlled by the sequencer 104.

In a case in which imaging is performed on a desired imaging region (imaging cross section) of a subject by the MRI apparatus 100 with the foregoing configuration, the computer 110 outputs an instruction to the sequencer 104 so that each unit of a measurement unit operates in accordance with a preset program and controls the operation of each unit included in the MRI apparatus 100. When the sequencer 104 sends commands to the gradient magnetic field power supply 105 and the high-frequency magnetic field generator 106, an RF pulse is applied to the subject 103 via the RF coil 107 at a timing and with an intensity instructed from the computer 110 and a gradient magnetic field pulse is applied by the gradient magnetic field coil 102. The gradient magnetic field is applied in order to provide positional information of slice selection, a phase encoding direction, and read-out direction to an echo signal, the gradient magnetic field pulses in orthogonal three-axis directions are appropriately combined to be used.

An NMR signal (echo signal) for generating nuclear magnetization in a tissue of the subject is received by the RF probe 108 and is detected (measured) by the receiver 109. The NMR signal is measured as digital data through time sampling for a predetermined sampling time and is disposed in a measurement space called a k space. The NMR signal is measured repeatedly until the k space is charged. The measured signal is sent to the computer 110. The computer 110 reconstructs an image by performing inverse Fourier transform on the signal charged in the k space. The storage device 112 stores the generated image and stores the detected signal, imaging conditions, and the like as necessary.

Of the programs executed by the computer 110, a program particularly describing application timings or intensities of the high-frequency magnetic field and the gradient magnetic field and a reception timing of a signal is called a pulse sequence. Imaging is performed in accordance with the pulse sequence and imaging parameters necessary to control the pulse sequence. By controlling the timings and the intensities of the high-frequency magnetic field and the gradient magnetic field set by the pulse sequence, it is possible to image any imaging cross section of a subject. The pulse sequence is generated in advance and retained in the storage device 112 and the imaging parameters are input via the input device 116 by the user. The computer 110 controls user interfaces of the input device 116, the display device 111, and the like, receives inputs, and causes the display device 111 to display the generated images.

Various pulse sequences are known according to purposes. For example, a gradient echo (GrE) type of high-speed imaging method is a method of sequentially changing a phase encoding gradient magnetic field at each repetition time (hereinafter referred to as a TR) of the pulse sequence and measuring the number of NMR signals necessary to obtain one tomographic image or a 3-dimensional image of a plurality of tomographic images. The imaging parameters include the repetition time TR, an echo time TE, a flip angle FA for determining the intensity of an RF pulse, and a radiation phase increment value $\theta$ of the RF pulse and can be set according to an image desired to be imaged.

By setting the pulse sequence or the imaging parameters according to physical properties desired to be weighted and imaged, it is possible to capture an image in which each of plurality of kinds of physical properties are weighted, for example, a T1-weighted image, a T2-weighted image, a fluid attenuated inversion recovery (hereinafter referred to as FLAIR) image, a magnetic susceptibility weighted image, and a diffusion weighted image. The physical properties include T1 (a longitudinal relaxation time), T2 (a transverse relaxation time), a PD (proton density), magnetic susceptibility, and a diffusion coefficient. By repeatedly capturing a weighted image a plurality of times while changing the imaging parameters and processing obtained signals, it is possible to calculate a plurality of physical properties of a tissue of a subject at the position of each pixel of the image. Thus, it is also possible to generate a quantitative image in which the physical property is set as a pixel value, that is, a T1 image in which T1 is set as a pixel value or a T2 image in which T2 is set as a pixel value. In the present specification, a weighted image and a quantitative image are collectively called a physical property dependent image.

By setting the pulse sequence and the imaging parameters of the TOF method, the PC method, or the like, a known MRA image can also, of course, be captured.

Embodiments of a process performed by the MRI apparatus according to the embodiment will be described based on the foregoing overview.

First Embodiment

A magnetic resonance imaging apparatus 100 according to the embodiment captures a plurality of images in which pulse sequences and imaging parameters are different to acquire a plurality of kinds of physical property dependent images. Then, the plurality of kinds of physical property dependent images are combined using predetermined combination parameters and a combination function to generate a combined image. The combination parameters are set such that pixel values of a specific tissue in the combined image are greater than pixel values of other tissues. The specific tissue is not limited. For example, a blood vessel is used. Thus, the physical property dependent images, which are diagnosis images of the tissues other than the specific tissue, and diagnosis images of the specific tissue, for example, an MRA image, can be acquired and displayed.

To realize this function, the computer 110 according to the embodiment includes an image acquisition unit 210, a combination parameter setting unit 220, a combined image generation unit 230, and a diagnosis image output unit 240 illustrated in FIG. 2. Specifically, the function of each unit is realized by software by allowing the CPU to read a program stored in advance in the memory of the computer 110 and execute the program. However, the computer 110 according to the embodiment is not limited to the computer realizing the function by the software. Some or all of the functions can also be realized by hardware such as a custom IC such as ASIC or a programmable IC such as FPGA. The image acquisition unit 210 includes the measurement unit besides a component included in the computer 110.

Hereinafter, an operation of the computer 110 according to the embodiment will be described in an example of a case in which a specific tissue is a blood vessel and a plurality of kinds of physical property dependent images are a PD weighted image and a T1 weighted image which are images for diagnosing a tissue other than the blood vessel. FIG. 3A illustrates a processing flow of the computer.

First, the image acquisition unit 210 receives an instruction from a user via the user interfaces (the display device 111 and the input device 116) and performs imaging in which the pulse sequences or the imaging parameters are different on an imaging region in a subject to acquire two or more kinds of physical property dependent images in which the weighted degree of the physical properties of the tissue other than the blood vessel and space distributions of pixel values inside the blood vessel are different (step S310).

Subsequently, the combination parameter setting unit 220 divides a predetermined region of interest into a plurality of division regions and sets a predetermined combination parameter at each division region (step S320).

Subsequently, the combined image generation unit 230 generates a combined image in the region of interest using the two or more kinds of images acquired in step S310 by the image acquisition unit 210, the combination parameters set in step S320 by the combination parameter setting unit 220, and a predetermined combination function (step S330).

The diagnosis image output unit 240 outputs one weighted image or a plurality of weighted images among the two or more weighted images acquired in step S310 by the image acquisition unit 210 as a diagnosis image of the tissue other than the blood vessel and outputs the combined image generated in step S330 by the combined image generation unit as the MRA image (step S340).

Hereinafter, a detailed process method of each unit will be described. Here, an example of a case in which an MRA image for diagnosing the shape of a blood vessel 401 of a human head 400 illustrated in FIG. 4(a) and a weighted image for diagnosing a tissue 402 other than the blood vessel of the human head 400 are simultaneously acquired will be described. Here, a direction from a neck to the top of the head (body axis direction) is defined to the Z axis. A lower end of the imaging region on the neck side is defined to Z=0. A plane vertical to the Z direction is assumed to be the XY plane.

[Step S310]

The image acquisition unit 210 sets an imaging region 403 at a predetermined region of the head 400 of the subject. Specifically, an image of the human head 400 acquired through imaging for positioning is displayed on the display device 400, a designation of a position by the user through the input device 116 is received and the imaging region 403 is set. The imaging region 403 may be identical or different in imaging performed a plurality of times, but is assumed to have a common region to form a combined image.

Subsequently, the image acquisition unit 210 captures a 3-dimensional image 411 and a 3-dimensional image 412 of the imaging region 403 as in FIG. 4(b) in accordance with a predetermined pulse sequence. Specifically, images in which the imaging parameters FA and TR are different are captured using a pulse sequence of a gradient echo. A PD weighted image 411 in which a difference in PD is weighted is acquired by setting a small FA (for example, 10°) and a long TR (for example, 40 ms) as a first imaging condition. A T1 weighted image 412 in which a difference in T1 is weighted is acquired by setting a large FA (for example, 20°) and a short TR (for example, 20 ms) as a second imaging condition.

FIG. 4(c) illustrates sectional views of the captured 3-dimensional images. A sectional view 421 of the 3-dimensional image 411 and a sectional view 422 of the 3-dimensional image 412 are a PD weighted image and a T1 weighted image which are image for diagnosing the tissue other than the blood vessel.

FIG. 4(d) illustrates projected views 431 and 432 of portions in which unnecessary regions such as a skin and the vicinity of a nasal cavity of the 3-dimensional images 411 and 412 are removed and which is obtained in accordance with a maximum intensity projection method. The projected views 431 and 432 of the 3-dimensional images are different in portions in which the blood vessel has high luminance and low luminance.

FIGS. 4(e) and 4(f) are graphs illustrating average luminance of the blood vessel and the tissue of the other blood vessel on the XY plane at each position in the Z direction in the 3-dimensional images 411 and 412 when the lower end of the imaging region is set to Z=0. As indicated by a dotted line in the drawing, the luminance of the tissue other than the blood vessel is substantially constant, but the luminance of the blood vessel indicated by solid line changes due to an influence of a flow. In particular, in the blood vessel of the head, blood mainly flows in the Z direction which is the direction from the neck to the top of the head. Therefore, the average luminance of the blood vessel considerably changes at each position in the Z direction. The change in the luminance in the Z direction depends on an imaging condition. In particular, in a case in which a gradient echo-based sequence is used, the change in the luminance considerably depends on FA and TR. Therefore, in FIGS. 4(e) and 4(f) in which FA and TR are changed in the imaging, a portion with higher luminance and a portion with lower luminance than the average luminance of the blood vessel are different in position in the Z direction in the blood vessel. That is the 3-dimensional images 411 and 412 have different space distributions of the pixel values inside the blood vessel.

As described above, the image acquisition unit 210 captures the images while changing the pulse sequence or the imaging parameters to acquire two or more kinds of physical property dependent images in which the weighted degree of the physical properties of the tissue other than the blood vessel and space distributions of pixel values inside the blood vessel are different.

In the pulse sequence, several methods such as a spin echo method and an inversion recovery method can be used in addition to the gradient echo method. However, since the TR can be set to be shorter than in other sequences, the gradient echo method is suitable in that the imaging time can be shortened. In the gradient echo method, the space distribution of the pixel value of the blood vessel can be considerably changed by changing FA for performing the imaging. Therefore, it is possible to obtain an image in which blood vessels of various parts can be easily identified in a combined image.

The imaging conditions of the image acquisition unit 210 may be changed to an echo time TE, an RF phase increment value θ, and the like in addition to FA and TR. Since the space distribution of the pixel values of the blood vessel is changed differently from FA and TR, there is an advantageous effect of easily separating the blood vessel in a broad range from the tissue other than the blood vessel in the combined image generation unit 230. In particular, in a case in which TE is changed for performing the imaging, a weighted image in which a difference in the apparent transverse relaxation time T2* is weighted can be obtained, and thus there is an advantageous effect of enabling diagnosis using a difference of T2*.

In a case in which the inversion recovery method is used as the pulse sequence, the inversion time TI is set as an imaging parameter. The inversion time TI may be changed for performing the imaging. Thus, it is possible to obtain an image (for example, an FLAIR image, a T2 weighted image, or the like) with the weighted degree of a stationary tissue different from in the gradient echo.

[Step S320]

The combination parameter setting unit 220 sets parameters (combination parameters) of a combination function used when the combined image generation unit 230 combines the plurality of physical property dependent images acquired in the foregoing step S310.

When Ic is a pixel value after the combination and $I_1$ and $I_2$ are pixel values of the combined physical property dependent images, the combination function can be generally described as Ic=f($I_1$, $I_2$). Here, a case in which a linear polynomial expression of the following Expression (1) is used as an example of a combination function will be described.

$$I_c = a \cdot I_1 + b \cdot I_2 + c \quad (1)$$

Here, a and b are coefficients and c is a constant, which are combination parameters set in this step.

Hereinafter, a detailed process of this step will be described with reference to FIG. 3B.

The combination parameter setting unit 220 first specifies a region of interest which is a combination parameter calculation target and divides the region of interest into a plurality of regions of interest (S321). Thereafter, the combination parameter is set at each of the plurality of division regions. The region of interest is preferably divided in a direction in which a difference occurs in the method of changing the luminance value of the blood vessel (specific tissue) between two images to be combined, as illustrated in FIGS. 4(e) and 4(f). For example, in the case of the blood vessel, the region of interest is preferably divided in a main traveling direction of the blood vessel (on a plane vertical to the traveling direction). FIG. 5(a) illustrates a form of the division of the region of interest. In the example of the drawing, a region of interest 500 inside the imaging region 403 set in the human head 400 is divided into N division regions 501-1 to 501-N in parallel to the XY plane. The region of interest 500 is all or a part of the imaging region and is set by setting a predetermined position inside an imaging region determined in advance or receiving an instruction from the user using a user interface. In a case in which imaging regions of the plurality of images are different, all or the part of the imaging region common to the plurality of images is set. A user's instruction of the direction of the division or the number of divisions may be received.

The combination parameter setting unit 220 sets combination parameters (a, b, and c) at each division region divided in this way (step S322). Specifically, the combination parameters are set so that the condition that the pixel value of the blood vessel after the combination is greater than the pixel value of the tissue other than the blood vessel is satisfied at each division region based on standard data of the pixel values of the blood vessel and the tissue other than the blood vessel of the image obtained by the image acquisition unit 210 and a representative value of the pixel value at each division region is a value common to all the division regions.

In the embodiment, in the plurality of kinds of images obtained by imaging the imaging region 403 by the image acquisition unit 210 under the same imaging condition as the imaging condition applied to the subject in a healthy volunteer in advance, data (preliminary pixel value data) of the pixel values of the blood vessel and the tissue other than the blood vessel is used as the standard data. Information (label) indicating whether a pixel is a pixel of the blood vessel or the tissue other than the blood vessel is given to the preliminary pixel value data. For example, the label information is set manually by imaging the imaging region 403 of the healthy volunteer in accordance with a scheme of the MRA of the related art such as the TOF method and viewing an acquired MRA image or may be set automatically using in the MRA image of the related art using a binarization process or the like. The label information is added to the preliminary pixel value data.

When a range of a value taken by a pair of pixel values $I_1$ and $I_2$ into the preliminary pixel value data is plotted for pixels of which a label is the blood vessel and pixels of which a label is the tissue other than the blood vessel, for example, the graph illustrated in FIG. 5($b$) is obtained. A range 511 of the pair of pixel values of the blood vessel and a range 512 of the pair of pixel values of the tissue other than the blood vessel are located at different locations on the plot. Since the range 512 of the pair of pixel values of the tissue other than the blood vessel includes a distribution of pixels of a plurality of biological tissues such as grey matter and white matter, the range has an extending form such as an ellipse.

The combination in which the combination function of the above-described Expression (1) is used means projection of the pair of $I_1$ and $I_2$ on an axis indicated by Ic in FIG. 5($b$). Thus, in a case in which the combination function is applied to $I_1$ and $I_2$ of the preliminary pixel value data, the combination parameter setting unit 220 determines a slope of the axis (Ic) so that value ranges taken by the pixel value Ic of the blood vessel and the tissue other than the blood vessel do not overlap each other as far as possible (step S322-1). The slope of the axis is determined as a ratio between the combination parameters a and b.

Specifically, a vector (a', b') indicating the ratio between a and b is first determined using a Fisher's linear discriminant analysis. (a, b) is determined to be proportional to (a', b').

$$\begin{pmatrix} a\prime \\ b\prime \end{pmatrix} = \Sigma^{-1} \cdot \begin{pmatrix} \mu_{1b} - \mu_{1o} \\ \mu_{2b} - \mu_{2o} \end{pmatrix} \quad (2)$$

In Expression (2), $\mu_{1b}$ and $\mu_{2b}$ are averages of the pixel values of the blood vessel in the pixel values $I_1$ and $I_2$, and $\mu_{1o}$ and $\mu_{2o}$ are averages of the pixel values of the tissue other than the blood vessel in the pixel values $I_1$ and $I_2$. $\Sigma$ is an in-class distribution expressed in Expression (3) below.

$$\Sigma = \frac{N_b \Sigma_b + N_o \Sigma_o}{N_b + N_o} \quad (3)$$

In Expression (3), Nb and No are numbers of pixels of the blood vessel and the tissue other than the blood vessel, and Σb and Σo are values obtained by dividing averages of variance-covariance matrices of the pair of pixel values ($I_1$, $I_2$) in the blood vessel and the tissue other than the blood vessel. A ratio (a', b') calculated using Expression (2) is known to be a ratio at which the value ranges taken by the pixel value Ic of the blood vessel and the tissue other than the blood vessel do not overlap as far as possible, that is, a difference in the pixel value Ic after the combination of the blood vessel and the tissue other than the blood vessel increases, when the length of the vector (a', b') is constant.

Subsequently, signs of a and b are determined so that the average of the pixel values of the blood vessel in the combined image (the pixel value Ic) is greater than the average of the pixel value of the tissue other than the blood vessel (step S322-2). Thus, in the combination function, the pixel values of the blood vessel can be set to be greater than the pixel values of the tissue other than the blood vessel. The case in which the condition that the pixel values of the blood vessel are set to be greater than the pixel values of the tissue other than the blood vessel at each division region is satisfied as the condition that the signs of the combination parameters a and b are determined has been described. Instead, the condition that the pixel values of the blood vessel are less than the pixel values of the tissue other than the blood vessel may be set to be satisfied. In this case, in a case in which the combined image output from the diagnosis image output unit 240 is displayed in accordance with a minimum value projection method, the blood vessel is displayed with black and the other tissue is displayed with white, and thus an apparent blood vessel image similar to a BSI image or the like can be obtained.

Subsequently, a, b, and c are determined so that the foregoing conditions (that is, the conditions of the ratio between a and b and the signs of a and b) are satisfied and the average and the variance of the pixel value Ic of the tissue other than the blood vessel are constant values (step S322-3). Hereinafter, a case in which the average is set to 0 and the variance is set to 1 will be described. First, a variance Sco of the pixel value Ic in the tissue other than the blood vessel in a case I which a' and b' are substituted as a and b to Expression (1) is expressed in Expression (4) below.

$$S_{co} = (a\prime b\prime) \cdot \Sigma_o \cdot \begin{pmatrix} a\prime \\ b\prime \end{pmatrix} \quad (4)$$

Accordingly, (a, b) by which the variance of the pixel value Ic of the tissue other than the blood vessel is set to 1 can be determined in accordance with Expression (5) below.

$$\begin{pmatrix} a \\ b \end{pmatrix} = \frac{1}{\sqrt{S_{co}}} \begin{pmatrix} a' \\ b' \end{pmatrix} \quad (5)$$

In addition, c is determined in accordance with Expression (6) below so that the average of the pixel value Ic of the tissue other than the blood vessel is 0.

$$c = -(a \, b) \cdot \begin{pmatrix} \mu_{10} \\ \mu_{20} \end{pmatrix} \quad (6)$$

By setting the average and the variance to 0 and 1 in this way respectively, the whole tissue other than the blood vessel has the low luminance (close to 0) and the range of the luminance in all the division regions is substantially constant, and thus it is possible to reduce the tissue other than the blood vessel, the tissue in which the high luminance is set erroneously as in the blood vessel.

In step S322-3, the average and the variance are set to be constant throughout all the division regions as the conditions for determining a, b, and c. However, instead of the average and the variance, a similar representative value, a median value, or an interquartile range indicating the value range of the pixel value Ic may be set to be constant (hereinafter, all of which are collectively referred to as a representative value).

In step S322-3, the combination parameter is determined based on the preliminary pixel value data so that the representative value is constant, but the combination parameters may be determined based on the physical property dependent image data used for the combination so that the representative value (for example, the average and the variance) are constant. Since the blood vessel is sufficiently smaller than the tissue other than the blood vessel, the average and variance of the tissue other than the blood vessel are substantially constant values. Compared to the case in which the combination parameters are determined using the preliminary pixel value data, there is the advantageous effect of obtaining an image which is rarely affected by an individual difference such as ratio or the like of various tissues included in the tissue other than the blood vessel.

The combination parameter setting unit 220 repeats the foregoing combination parameter setting process (S322-1 to S322-3) on the division regions 501-1 to 501-N(S323) to calculate the combination parameters at each of the division regions. As illustrated in FIGS. 4(e) and 4(f), the pixel values $I_1$ and $I_2$ of the blood vessel are considerably changed in the Z direction. Even for the tissue other than the blood vessel, the ranges of the pixel values $I_1$ and $I_2$ are changed to some extent since ratios of the included tissues are changed. Therefore, the combination parameters suitable to generate the combined image are different at each division region according to the position in the Z direction. By obtaining the combination parameters for setting considerably higher luminance of the blood vessel than that of the tissues other than the blood vessel and setting the higher luminance at the each division region, it is possible to improve precision of the combined image.

The combination parameter setting unit 220 may further perform a smoothing process between the regions after setting the combination parameters of each division region, as indicated by a dotted line in FIG. 3B (S324). For example, there is a moving average processing method of setting an average of parameter values in a division region adjacent to a certain division region as a new parameter. Thus, the combination parameter can be prevented from being abruptly changed between the regions, and thus there is the advantageous effect of smoothing the combined image. However, this step is not requisite.

Since the preliminary pixel value data used by the combination parameter setting unit 220 may be data indicating a range of standard pixel values at each division region, for example, the preliminary pixel value data of the adjacent division region 501-2 may also be used together as the preliminary pixel value data of the division region 501-1. In this way, the preliminary pixel value data of a certain division region may also include the preliminary pixel value data of a plurality of nearby division region. Thus, even in a case in which the preliminary pixel value data is small, it is possible to reduce a variation in the combination parameters set at each division region.

[Step S330: FIG. 3]

The combined image generation unit 230 generates the combined image from the physical property dependent images 411 and 412 of the subject acquired by the image acquisition unit 210 and the combination parameters set at each division region by the combination parameter setting unit 220. Specifically, the pixel values $I_1$ and $I_2$ of the same pixels between two images acquired by the image acquisition unit 210 at each pixel of the imaging region 403 and the combination parameters a, b, and c set in the partial region 501-n including the pixels among the partial regions 501-1 to 501-N by the combination parameter setting unit 220 are substituted to Expression (1) to set pixel values of the combined image in the pixels.

Thus, it is possible to obtain a combined image 521 in which the whole blood vessel can be ascertained, as in the image illustrated in FIG. 5(c). Actually, the combined image 521 is a 3-dimensional image, but a projected view is illustrated with maximum intensity projection (MIP) for description.

[Step S340]

First, the diagnosis image output unit 240 outputs the physical property dependent images 411 and 412 acquired by the image acquisition unit 210 as a PD weighted image and a T1 weighted image for diagnosing the tissue other than the blood vessel, respectively. For example, an instruction is received from the user and any cross section of each of the physical property dependent images 411 and 412 are displayed as outputs on the display device 111.

Subsequently, the diagnosis image output unit 240 outputs the combined image 512 generated by the combined image generation unit 230 as an MRA image for diagnosing the blood vessel. For example, a 2-dimensional image of the combined image subjected to the MIP in predetermined direction is displayed as an output on the display device 111.

Any display method may be used. A plurality of images may be displayed in parallel, or one image or a plurality of images may be displayed on demand from the user.

Instead of displaying the images on the display device 111 of the MRI apparatus 100 or in conjunction with the display of the images, the images may be output to be transmitted as image data to a display device, a storage device, or the like independent from the MRI apparatus 100.

According to the embodiment, the MRA image and a plurality of weighted images in which the structure of the tissue other than the blood vessel can be ascertained can be simultaneously acquired without performing imaging for MRA apart from the acquisition of the physical property dependent image. Thus, it is possible to shorten an examination time. According to the embodiment, since an image to be used for combination is divided into a plurality of regions and the combination parameters to be used for the combination are determined at each division region, a ratio which is different at each division region and a ratio of the pixels between the blood vessel and the tissue other than the blood vessel, a difference in the pixel value, or the like can be reflected in the combination parameters. Thus, it is possible to supply a combined image (MRA image) with high precision.

In the embodiment, as the region division method, the region of interest 500 is divided on a cross section nearly vertical to the direction in which blood mainly flows. The pixel values of the blood vessel are changed in the direction in which blood flows. Therefore, by setting the division regions to be vertical to the direction in which blood mainly flows, it is possible to set the combination parameters suitable for weighting the blood vessel. Since a 3-dimensional image generally has a data structure in which a plurality of 2-dimensional cross sectional images are collected, there is the advantageous effect in which calculation cost is small in the division of the region for each cross sectional image. However, the region division method is not limited to the foregoing method. For example, a region may be divided in different division regions from those of the embodiment, for example, by setting a plurality of division regions further divided on a plane of a cross section. In this case, there is the advantageous effect in which combination parameters more suitable for each partial region can be set.

Further, in the embodiment, the case in which the image acquisition unit 210 performs imaging under the two imaging conditions has been described. However, an image can, of course, be captured under three or more imaging conditions. In this case, the combination function is a linear polynomial of many pixel values and the combination parameters are coefficient and constant terms of the linear polynomial. By combining many images, it is possible to combine MRA images in which the blood vessel and the tissue other than the blood vessel are more clearly divided.

In addition to the steps indicated by solid lines in the flow of FIG. 3A, another process for correction can also be added. For example, as indicated by a dotted line in FIG. 3A, the image acquisition unit 210 applies a correction process (S315) on acquired weighted images, which can be used as new physical property dependent images in steps S330 and S340.

As an example of the correction process, the image acquisition unit 210 may apply a normalization process, such as constant multiplication and constant subtraction in which the average of the pixel values is 0 and the variance of the pixel values is a fixed value (for example, 1), on the acquired physical property dependent images to generate new physical property dependent images. Thus, there is the advantageous effect in which the ranges of the pixel values of each image are unified and a calculation error of the combination parameters in the combination parameter setting unit can be reduced. Alternatively, an image of which sensitivity is corrected may be generated as a new physical property dependent image by smoothing one of the acquired physical property dependent images to set a sensitivity map in which a sensitivity distribution in an imaging region is estimated and dividing one physical property dependent image or each of the plurality of physical property dependent images with the sensitivity map. Thus, it is possible to obtain a diagnosis image of the tissue other than the blood vessel and an MRA image in which sensitivity irregularity is reduced.

Further, the case in which the designation of the position by the user is received in regard to the imaging region has been described above. The combination parameters with which the blood vessel is well separated from the tissue other than the blood vessel in each division region differ depending on a part of the subject in which the imaging region is located. For this reason, the imaging region may be fixed in advance using the structure of a human body common to the subject as a reference. For example, there is a method of determining a rectangular parallelepiped with a height of 15 cm as an imaging region by setting a great foramen which is a lower part of a cranial bone as a lower end.

In several cases in which the position at which the imaging region is set is different for the preliminary pixel value data, each preliminary pixel value may be stored and the combination parameter setting unit may select the preliminary pixel value data according to the set imaging region and use the preliminary pixel value to set the combination parameters. Thus, it is possible to combine better MRA images in accordance with the imaging region desired to be imaged by the user.

Second Embodiment

In the embodiment, the configuration of the computer 110 is also the same as the configuration illustrated in FIG. 2. In the first embodiment, the combination parameter setting unit 220 sets the combination parameters using the preliminary pixel value data of the blood vessel and the tissue other than the blood vessel at each of the division region acquired in advance setting a volunteer as a target. In the embodiment, however, preliminary pixel value data generated imaginarily using a simulation or the like is used instead of imaging a volunteer in advance. The other steps are the same as those of the first embodiment. Hereinafter, differences from the first embodiment will be mainly described.

The preliminary pixel value data is generated by requesting calculation or simulation of signal values of NMR signals. In general, when PD, T1, and T2 of a biological tissue and a distribution of an RF radiation intensity B1 in an imaging region are known, the signal values of the NMR signals can be calculated for each echo using TR and FA which are imaging parameters, and theoretical values of signal intensities of a moving tissue such as blood and a stationary tissue other than blood can be obtained.

For example, when M0 is an initial value of longitudinal magnetization and Mn is longitudinal magnetization immediately before an n-th RF pulse in a signal value of a gradient echo, longitudinal magnetization immediately before an n+1-th RF pulse can be expressed in Expression (7).

$$M_{n+1} = M0 - (M0 - M_n \cdot \cos(B1 \cdot FA)) \cdot \exp\left(-\frac{TR}{T1}\right) \quad (7)$$

In addition, a signal intensity In of an n-th echo is expressed in Expression (8).

$$I_n = M_n \cdot \sin(B1 \cdot FA) \quad (8)$$

A signal intensity I of a stationary tissue other than a blood vessel can be approximated as a limit in Expression (9) below when n→∞ in Expression (8) above.

$$I(PD, T1, B1, TR, FA) = \frac{PD \cdot \sin(B1 \cdot FA)\left\{1 - \exp\left(-\frac{TR}{T1}\right)\right\}}{1 - \cos(B1 \cdot FA)\exp\left(-\frac{TR}{T1}\right)} \quad (9)$$

Here, an influence of T2 is ignored as TE=0. Transverse magnetization after an echo is gradually attenuated until a subsequent RF pulse or is assumed not to remain, for example, by adding a gradient magnetic field pulse to cancel the transverse magnetization.

By calculating the luminance of blood at a point of any position in an imaging region using Expression (8) for each echo until the blood flows and arrives at the point, it is possible to theoretically calculate luminance (pixel value) at that point. In a human head, blood mainly flows in the Z direction. Therefore, by assuming that a blood vessel in a straight form from the lower end to the upper end of the imaging region, an approximate value with the signal intensity of the blood traveling at a constant flow rate can be obtained.

However, in practice, PD, T1, T2, or a flow rate varies within a fixed range. A signal intensity to be measured includes noise. Accordingly, pixel value data of a blood vessel and other tissues may be generated, for example, by preparing a plurality of patterns of PD, T1, T2, and the flow rate and obtaining signal intensities or artificially adding noise to the signal intensities. The pixel value data may be set as preliminary pixel value data to be used by the combination parameter setting unit 220.

After the preliminary pixel value data is acquired in this way, the preliminary pixel value data is divided to a plurality of regions, the combination parameter is determined at each division region, the determined combination parameter is applied to the combination function, the plurality of physical property dependent images obtained by imaging a subject are combined to generate a combined image which is an image for blood vessel diagnosis, as in the first embodiment.

According to the embodiment, there is the advantageous effect in which it is not necessary to image volunteer data in advance in addition to the same advantageous effects as those of the first embodiment.

Third Embodiment: Modification Example of Combination Function

In the first embodiment, the coefficients are calculated as the combination parameters using the linear polynomial as the combination function. However, the combination function is not limited to the linear polynomial. A discriminant function of receiving inputs of a pair of pixel values and outputting values indicating a blood vessel or a tissue other than the blood vessel may be used and the combination parameters may be parameters of the discriminant function. As the discriminant function, for example, a known scheme such as a neural network, a support vector machine, or a nearest neighbor algorithm can be adopted. As in the first embodiment, the parameters of the discriminant function are determined so that value ranges which can be taken by pixel values of the blood vessel and the tissue other than the blood vessels in a combined image can be separated as far as possible. Thus, it is possible to obtain the same advantageous effects as those of the first embodiment. When the linear polynomial is used, there is the advantageous effect of reducing calculation cost necessary to calculate the combination parameters. By using another discriminant function, there is the advantageous effect of obtaining an MRA image in which noise is less.

Further, a function (probability function) of calculating a probability at which a certain point is a blood vessel can also be used as the combination function. Hereinafter, an embodiment of a case in which the probability function is used will be described. The configuration of a computer according to the embodiment is the same as the configuration of the computer exemplified in FIG. 2 according to the first embodiment. The combined image generation unit 230 uses an expression indicating a probability of the blood vessel and the tissue other than the blood vessel as the combination function. The combination parameter setting unit 220 sets parameters of a model indicating a probability of the blood vessel and the tissue other than the blood vessel as the combination parameters.

Hereinafter, the description will be made appropriately with reference to FIG. 3B illustrating the flow of the first embodiment.

In the embodiment, as in the first or second embodiment, the preliminary pixel value data is acquired by volunteer data imaging or simulation as a premise. Subsequently, the preliminary pixel value data is divided into a plurality (1 to N) of regions (S321). Thereafter, a combination parameter is calculated at each division region (S322). Here, a combination parameter of a probability f (a combination function) at which a certain pixel is a blood vessel is calculated as a combination parameter.

Hereinafter, a case in which a probability at which a certain pixel is a blood vessel is calculated from the pixel values $I_1$ and $I_2$ will be described.

The probability f at which a certain pixel is a blood vessel can be expressed in Expression (10) below using an average and a variance of pixel values of pixels of the blood vessel and an average and a variance of pixel values of a tissue other than the blood vessel.

$$f(x, a, \mu_b, \Sigma_b, \mu_o, \Sigma_o) = \frac{a \cdot p(x, \mu_b, \Sigma_b)}{a \cdot p(x, \mu_b, \Sigma_b) + (1-a) \cdot p(x, \mu_o, \Sigma_o)} \quad (10)$$

In the expression, μb and Σb are the average and the variance of the pixel values of the blood vessel, μo and Σo are the average and the variance of the pixel values of the tissue other than the blood vessel, and a is a ratio of the pixels of the blood vessel to all the pixels. Here, a, μb, Σb, μo, and Σo are combination parameters calculated herein.

In addition, p is a probability density function. For example, when the pixel values $I_1$ and $I_2$ of the blood vessel and the tissue other than the blood vessel conform to a multivariate normal distribution, the probability density function p of the multivariate normal distribution can be expressed in Expression (11).

$$p(x, \mu, \Sigma) = (2\pi)^{-\frac{m}{2}} |\Sigma|^{-\frac{1}{2}} \cdot \exp\left(-\frac{1}{2}(x-\mu)^T \Sigma^{-1}(x-\mu)\right) \quad (11)$$

In the expression, μ is an average, Σ is a variance-covariance matrix (variance), x is a vector indicating a pair of pixel values ($I_1, I_2, \ldots$) used for combination, and m is the number of dimensions of x, that is, the number of kinds of images used for combination.

The combination parameter setting unit 220 calculates the combination parameters of Expression (10) based on the preliminary pixel value data of a plurality of kinds of images. Specifically, in each division region of the preliminary pixel value data, the pixels of the blood vessel and the pixels of the tissue other than the blood vessel are determined using determination information acquired in advance as in the first embodiment, and the ratio (the combination parameter a) of the pixels of the blood vessels to all the pixels is calculated. Each average and each variance of the determined pixels of the blood vessel and the determined pixels of the tissue other than the blood vessel are calculated. As x, the pair of pixel values of the preliminary pixel value data of the plurality of kinds of images is used.

The combination parameter setting unit 220 repeats the process of calculating the foregoing combination parameters on all the division regions (step S323) and the combination parameter setting step is completed.

The combined image generation unit 230 calculates the probability f at which a certain pixel is a blood vessel, using the combination parameters calculated by the combination parameter setting unit 220 and the pixel values of the plurality of kinds of images obtained by actually imaging the subject as x in Expressions (10) and (11). In the image in which the probability calculated in this way is set as a pixel value, the pixel value of the blood vessel is close to 1 and the pixel value of the tissue other than the blood vessel is almost 0. Therefore, a blood vessel can be captured as a high-luminance MRA image and can be used as a combined image without change.

Further, as indicated in Expression (12) below, quality can be further improved by adding combination parameters u and v.

$$IC = u \cdot f(x, a, \mu_b, \Sigma_b, \mu_{\bar{b}}, \Sigma_{\bar{b}}) + v \quad (12)$$

The combination parameters u and v can be uniquely determined so that the average and the variance of the tissue other than the blood vessel are 0 and 1, respectively.

In the embodiment, as in the first and second embodiments, an image with an excellent visualization ability of a specific tissue such as a blood vessel apart from the physical property dependent images can be generated to be displayed from the plurality of physical property dependent images without separately performing MRA imaging.

In the embodiment, the case in which the probability function is used as an example of the combination function other than the linear polynomial has been described. Additionally, a method of using a Sigmoid function as the function of calculating the probability of the blood vessel and setting parameters of the Sigmoid function as the combination parameters using logistic regression can be adopted.

Fourth Embodiment

Next, a fourth embodiment of the invention will be described. In the fourth embodiment, an MRI apparatus has basically the same configuration as that of the MRI apparatus according to the first to third embodiments is used. Unlike the first to third embodiments, the MRI apparatus has a function of calculating a quantitative image with which diagnosis can be performed using physical properties.

Specifically, the computer 110 according to the embodiment further includes a quantitative image calculation unit 610, as illustrated in FIG. 6. Hereinafter, a process according to the embodiment will be described focusing on differences from the first embodiment.

FIG. 7 illustrates an overview of a process according to the fourth embodiment. The image acquisition unit 210 acquires a plurality of physical property dependent images by performing imaging using a predetermined pulse sequence (step S310). The quantitative image calculation unit 610 calculates a physical property for each pixel in an imaging region from a captured image and calculates a quantitative image in which the physical proprieties are the pixel values (step S710). The combined image generation unit 230 performs image combination using one or both of the physical property dependent image captured by the image acquisition unit 210 and the quantitative image calculated by the quantitative image calculation unit 610 (S330). Before the combination, the combination parameter setting unit 220 sets the combination parameters to be used by the combined image generation unit 230 (S320). The quantitative image is a physical property dependent image in which a difference in the physical property of the tissue other than the blood vessel is also reflected and a pixel value of the blood vessel differs depending on a location due to an influence of a flow. Accordingly, by combining the quantitative image with the appropriate combination parameters, it is possible to generate an MRA image with an excellent ability to represent the blood vessel.

Hereinafter, the details of the process will be described with reference to FIG. 8.

<Step S310>

The image acquisition unit 210 acquires a plurality of physical property dependent images 801. As the pulse sequence, it is preferable to use a gradient echo-based pulse sequence. Another pulse sequence, for example, a pulse sequence such as a spin echo method, an inversion recovery method, or a diffusion weighted image method, may be used.

Specifically, imaging is performed using a pulse sequence in which combinations of imaging parameters TR, TE, FA, and θ are different and the remaining conditions are the same or a pulse sequence in which a plurality of echoes with different TE are acquired in one pulse sequence, and N kinds of different weighted images 801-1 to 801-N in which combinations of TR, TE, FA, and θ are different are acquired.

As the combinations of the imaging parameters, it is preferable to capture three kinds or more of weighted images in which TR or FA is different suitably and capture four kinds or more of weighted images more suitably in addition to a condition of an imaging parameter in which TE or θ is different. Thus, in calculation of quantitative value to be described below, three unknown PD, T1, and B1 or four unknown PD, T1, T2, and B1 can be obtained at a time by fitting. Compared to a case of two kinds of weighted images, images used by the combined image generation unit 230 can be increased, and thus there is the advantageous effect of improving the quality of the MRA image. More suitably, it is preferable to increase imaging conditions in which TR, FA, TE, and θ are different and capture five or more kinds of weighted images. Since captured images are more than the kinds of calculated quantitative images, an influence of noise in the fitting is small, and thus there is the advantageous effect of obtaining quantitative images with small noise.

<Step S710>

The quantitative image calculation unit 610 estimates a physical property from the weighted image for each pixel in the imaging region, using a luminance function indicating a relation among the imaging parameter, the physical property, and the luminance in the pulse sequence used for the imaging. In the estimation, a quantitative value is calculated by performing least square fitting on the luminance function at the imaged luminance and the imaging condition. As the luminance function, since there is an existing luminance function in the pulse sequence of the spin echo method, the inversion recovery method, or the gradient echo method (for example, the above-described Expression (7) or the like), the existing luminance function can be used. Since an analytic luminance function such as RF Spoiled Steady State Gradient Echo (RSSG) is complex, a luminance function may be generated by simulation in a high-speed imaging sequence on which it is difficult to perform fitting. By performing fitting on the luminance function at the luminance and the imaging condition of the captured image, it is possible to obtain the physical property.

As a scheme other than the fitting of the luminance function, there is a method of generating a database directly indicating a relation between the physical property and the luminance in advance by simulation and obtaining the physical property by matching, and thus either method can be adopted.

By calculating a quantitative value for each pixel, it is possible to obtain a quantitative image in which the quantitative value is the pixel value. As the calculated quantitative images, for example, there are a PD image 802-1, a T1 image 802-2, and a T2 image 802-3. An RF radiation intensity B1 in a subject can also be calculated.

<S320 to S340>

The combination parameter setting unit 220 determines the combination parameters at the time of combining the plurality of images in accordance with the same scheme as that of the first embodiment. The physical property dependent images to be used for the combination include not only a weighted image captured using the pulse sequence by the image acquisition unit 210 and the quantitative image acquired by the quantitative image calculation unit 610 but also an image obtained through further calculation from these images. For example, the weighted image can be generated with a theoretical expression of the luminance of the following spin echo from the PD image, the T1-value image, and the T2-value image which are quantitative images.

$$I(PD, T1, T2, TR, TE) = PD \cdot \left\{1 - \exp\left(-\frac{TR}{T1}\right)\right\} \cdot \exp\left(-\frac{TE}{T2}\right) \quad (13)$$

In Expression (13), TR and TE are imaging parameters. By changing TR and TE for calculation, it is possible to generate various weighted images. Here, the theoretical expression of the luminance of the spin echo is used, but any function of outputting a value depending on the physical property, for example, any of various functions such as an exponential function, a logarithmic function, a trigonometric function, a Gauss function, a Sigmoid function, and a polynomial and a combination thereof, can be used. By changing the function, it is possible to calculate images in which the weighted degree is different.

Two or more of the images can be arbitrarily assembled and combined. The combination parameter setting unit 220 sets the combination parameter using standard data corresponding to a pair of combined images. A combination of images to be combined may be designated by the user or a system may be determined in conformity with the standard data acquired in advance.

The combined image generation unit 230 combines the designated or determined combination of the images using the combination parameters set by the combination parameter setting unit 220 (S330). The diagnosis image output unit 240 outputs the combined image and another physical property dependent image, the quantitative image, or a calculated image as images for diagnosis to, for example, the display device 111 (S340). Thus, it is possible to output various diagnosis images of the tissue other than the blood vessel in which the weighted degree is different.

The quantitative image is helpful to ascertain and diagnose a structure of grey matter and white matter and enables quantitative evaluation of a disease. It is known that various diagnosis images can be combined in postprocessing from the physical properties. According to the embodiment, it is possible to simultaneously acquire the quantitative image and the MRA image, and thus it is possible to expect to additionally shorten an examination time.

The case in which the image acquisition unit 210 according to the embodiment performs the imaging in the measurement unit under the imaging conditions in which the imaging parameters TR, FA, TE, and θ are different using the gradient echo-based pulse sequence and calculates PD, T1, T2, and B1 has been described. Various cases of the pulse sequence used by the image acquisition unit 210, the imaging parameters changed in each imaging, and the physical properties to be calculated are additionally considered.

The imaging parameters such as the inversion time T1 in the case in which the inversion recovery method is used and a b value of the pulse sequence of the diffusion weighted image method may be changed. By changing T1, it is also possible to calculate T1. By changing the b value, it is possible to obtain the plurality of diffusion weighted images in which dependency on the diffusion coefficient is different, and thus it is possible to calculate an apparent diffusion coefficient ADC for each pixel.

Fifth Embodiment

In a fifth embodiment, an MRI apparatus has basically the same configuration as the MRI apparatus according to the first embodiment, but has a function in which a user can adjust the combination parameters to combination parameters suitable for each subject unlike the first embodiment.

Specifically, the computer 110 according to the embodiment further includes a combination parameter adjustment unit 910, as illustrated in FIG. 9, in addition to the configuration in FIG. 2.

Hereinafter, a processing flow according to the embodiment will be described focusing on differences from the first embodiment. The processing flow according to the fifth embodiment is illustrated in FIG. 10.

As illustrated in FIG. 10, when the image acquisition unit 210 acquires the plurality of physical property dependent images (step S310) and the combination parameter setting unit 220 sets the combination parameters (step S320), the combination parameters are stored in the storage device 112 or a memory of the computer 110. The combination parameter adjustment unit 910 receives an input via a user interface after the setting of the combination parameters and adjusts the combination parameters set by the combination parameter setting unit 220 according to the input (step S1010). The adjusted parameters are newly stored in the storage device 112 and the combination parameter setting unit 220 performs image combination using the combination parameters (step S330).

The operation (S1010) of the combination parameter adjustment unit 910 will be described in detail with reference to FIG. 11.

The combination parameter adjustment unit 910 first displays a combination parameter adjustment screen 1100 on the display device 111. The combination parameter adjustment screen 1100 includes, for example, a combination parameter display region 1101 in which the combination parameters are visually displayed, an adjustment reception region 1102 in which adjustment of the combination parameters desired to be performed by the user is received, and an adjustment completion instruction reception region 1103 in which an adjustment completion instruction is received. In the combination parameter display region 1101, for example, a graph plotted in each division region is displayed in each of parameters a, b, and c, here, the division regions are divided in the Z direction. Therefore, the horizontal axis corresponding to the division region represents the Z direction.

Subsequently, in the combination parameter adjustment reception region 1102, a numerical value change such as addition or multiplication of a constant in each of the parameters a, b, and c and an adjustment instruction such as translation of a corresponding division region are received through a mouse operation or the like of the input device 116. In the combination parameter adjustment reception region 1102 of FIG. 11, an example is shown in which a slide bar for receiving a mouse operation of instructing a constant for constant multiplication of a and b and a slide bar for receiving translation of the corresponding division region are displayed. The constant multiplication is d by which a assigned to all the division regions is multiplied when the user designates magnification of a as d. The translation is an operation of shifting the corresponding region in the Z direction. For example, when the user instructs a movement amount m (where m is the number of division regions), the combination parameter assigned to an n-th (=1 to N) division region in the Z direction is assigned to an (n+m)-th division region. In the division region in which there is no combination parameter assigned by movement, the parameter is assigned through an extrapolation process.

In a case in which an adjustment instruction from the user is received in the combination parameter adjustment reception region 1102 to adjust the combination parameter, the combination parameter adjustment unit 910 displays the newly allocated combination parameter in the combination parameter display region 1101. The adjustment instruction is received until the adjustment completion instruction from the user is received in the adjustment completion instruction reception region 1103.

In a case in which the adjustment completion instruction from the user is received in the adjustment completion instruction reception region 1103, step S1010 ends and the newly set combination parameter is used to generate the combined image in step S330.

As described above, in the MRI apparatus 100 according to the embodiment, the user can adjust the combination parameter to the combination parameter suitable for each subject.

The combination parameter display region 1101 according to the embodiment may serve as some or all of the functions of the adjustment reception region 1102. In this case, for example, by configuring some or all of the graphs of the combination parameters displayed in the combination parameter display region 1101 so that the user can move some or all of the graphs can be moved through a mouse operation and setting values of the combination parameters so that a graph shape designated by the user is formed, it is possible to adjust the combination parameters in forms which it is easy for the user to visually understand.

The embodiments of the MRI apparatus according to the invention have been described, but the invention is not limited to the embodiments. Various modifications such as addition or deletion of additional elements or combinations of the embodiments can be made.

In each embodiment, the case in which the specific tissue is mainly the blood vessel and the MRA image for diagnosing the shape of the blood vessel and the physical property dependent image for diagnosing the tissue other than the blood vessel are output has been described. However, in addition to the blood vessel, an image for diagnosing the shape of any specific tissue and a physical property dependent image for diagnosing a tissue other than the specific tissue can also be output. Instead of the blood vessel, for example, a target tissue such as grey matter, white matter, or a cerebrospinal fluid can be set. For example, in a case in which white matter is set as a target, both an image in which only white matter has high luminance and a physical property dependent image can be simultaneously acquired.

REFERENCE SIGNS LIST

100 MRI apparatus
101 magnet
102 gradient magnetic field coil
103 subject
104 sequencer
105 gradient magnetic field power supply
106 high-frequency magnetic field generator
107 RF coil
108 RF probe
109 receiver
110 computer
111 display device
112 storage device
113 shim coil
114 shim power supply
115 bed
116 input device
210 image acquisition unit
220 combination parameter setting unit
230 combined image generation unit
240 diagnosis image output unit
610 quantitative image calculation unit
910 combination parameter adjustment unit

The invention claimed is:

1. A magnetic resonance imaging apparatus comprising:
an image acquisition unit that measures a nuclear magnetic resonance signal in accordance with a predetermined pulse sequence under a plurality of imaging conditions to acquire two or more kinds of images;
a combined image generation unit that combines the two or more kinds of images using a predetermined combination parameter and a combination function to generate a combined image; and
a combination parameter setting unit that sets a combination parameter to be used by the combined image generation unit,
wherein the combination parameter setting unit sets a plurality of division regions in the images acquired by the image acquisition unit and sets the combination parameter satisfying a condition that a difference between a pixel value of a specific tissue and a pixel value of a tissue other than the specific tissue is large based on standard data of the two or more kinds of images at each of the division regions,
wherein the combination function is a discriminant function of outputting a value indicating the specific tissue or a tissue other than the specific tissue, and wherein the combination parameter setting unit sets the combination parameter so that a condition that a representative value of pixel values in the division regions is a common value to all the division regions is satisfied.

2. The magnetic resonance imaging apparatus according to claim 1,
wherein the specific tissue is a blood vessel and the combined image is an image for blood vessel diagnosis.

3. The magnetic resonance imaging apparatus according to claim 2,
wherein the combination parameter setting unit sets regions obtained by dividing an imaging region on each cross section vertical to a direction in which blood mainly flows as the division regions.

4. The magnetic resonance imaging apparatus according to claim 1,
wherein the image acquisition unit performs imaging under conditions in which at least one of a flip angle, a repetition time, an echo time, and a high-frequency magnetic field pulse phase increment value is different as the plurality of imaging conditions.

5. The magnetic resonance imaging apparatus according to claim 4,
wherein the pulse sequence used by the image acquisition unit is a gradient echo-based sequence, and
wherein the image acquisition unit performs the imaging under two or more conditions that at least one of the flip angle and the repetition time is changed as the plurality of imaging conditions.

6. The magnetic resonance imaging apparatus according to claim 1,
wherein at least one of the images acquired by the image acquisition unit is an image in which a difference in one of a proton density, a longitudinal relaxation time, and a transverse relaxation time of the tissue other than the specific tissue is weighted.

7. The magnetic resonance imaging apparatus according to claim 1,
wherein the representative value of the pixel values is an average and a variance or a median value and an interquartile range.

8. The magnetic resonance imaging apparatus according to claim 1,
wherein the discriminant function is a linear polynomial, and
wherein the combination parameter is a coefficient and a constant term of the linear polynomial.

9. The magnetic resonance imaging apparatus according to claim 1,
wherein the combination function is a function of calculating a probability of the specific tissue, and
wherein the combination parameter is a parameter of the function of calculating the probability.

10. The magnetic resonance imaging apparatus according to claim 1,
wherein the standard data is data of a pixel value of each of the specific tissue and the tissue other than the specific tissue at each of the division regions acquired by imaging a plurality of subjects in advance using the predetermined pulse sequence or simulating the pixel values obtained in the predetermined pulse sequence.

11. The magnetic resonance imaging apparatus according to claim 1, further comprising:
a quantitative image calculation unit that calculates a quantitative image from the plurality of images captured in the predetermined pulse sequence.

12. The magnetic resonance imaging apparatus according to claim 11,
wherein the quantitative image calculation unit further has a function of calculating a weighted image from the quantitative image.

13. The magnetic resonance imaging apparatus according to claim 1, further comprising:
a combination parameter adjustment unit that receives an input from a user and adjusts the combination parameter set by the combination parameter setting unit.

14. A magnetic resonance image processing method of combining two or more kinds of physical property dependent images obtained from a nuclear magnetic resonance signal measured in accordance with a predetermined pulse sequence under a plurality of imaging conditions, using a predetermined combination function and a combination parameter and generating a combined image which is a diagnosis image of a specific tissue, the method comprising:
setting a plurality of division regions in the physical property dependent image;
setting the combination parameter satisfying a condition that a difference between a pixel value of the specific tissue and a pixel value of a tissue other than the specific tissue increases at each of the division regions in the two or more kinds of physical property dependent images acquired by measuring the nuclear magnetic resonance signal, using standard data of the two or more kinds of physical property dependent images; and
generating a combined image using the combination parameter and the combination function;
wherein the combination function is a discriminant function of outputting a value indicating the specific tissue or a tissue other than the specific tissue, and
wherein the combination parameter is set so that a condition that a representative value of pixel values in the division regions is a common value to all the division regions is satisfied.

* * * * *